United States Patent
Sayegh

(10) Patent No.: US 10,398,544 B2
(45) Date of Patent: Sep. 3, 2019

(54) METHODS FOR SELECTING INTRAOCULAR LENSES AND RELAXING INCISIONS FOR CORRECTING REFRACTIVE ERROR

(71) Applicant: Samir I Sayegh, Champaign, IL (US)

(72) Inventor: Samir I Sayegh, Champaign, IL (US)

( * ) Notice: Subject to any disclaimer, the term of this patent is extended or adjusted under 35 U.S.C. 154(b) by 477 days.

(21) Appl. No.: 15/131,713

(22) Filed: Apr. 18, 2016

(65) Prior Publication Data
US 2016/0302915 A1   Oct. 20, 2016

Related U.S. Application Data

(60) Provisional application No. 62/149,539, filed on Apr. 18, 2015.

(51) Int. Cl.
*A61F 2/16* (2006.01)
*G02C 7/02* (2006.01)

(52) U.S. Cl.
CPC ...... *A61F 2/1645* (2015.04); *A61F 2240/002* (2013.01); *G02C 7/027* (2013.01)

(58) Field of Classification Search
None
See application file for complete search history.

(56) References Cited

U.S. PATENT DOCUMENTS

| | | |
|---|---|---|
| 7,476,248 B2 | 1/2009 | Harris et al. |
| 8,231,643 B2 | 7/2012 | Davis |
| 8,919,364 B1 | 12/2014 | Russel |
| 9,259,149 B2 | 2/2016 | Holladay et al. |
| 9,271,829 B2 | 3/2016 | Buhren et al. |
| 2005/0225721 A1 | 10/2005 | Harris et al. |
| 2015/0046094 A1* | 2/2015 | Chaudhary ........... A61F 2/1645 702/19 |

* cited by examiner

*Primary Examiner* — Leslie Lopez
(74) *Attorney, Agent, or Firm* — Wendy Thai

(57) ABSTRACT

The disclosure provides a method for selecting toric intraocular lenses (IOL) and relaxing incision for correcting refractive error. The one or more toric IOL and relaxing incision combinations can be used for off-axis correction of refractive errors such as astigmatism. The disclosure provides a method for selecting toric IOL and relaxing incision combinations that have combined astigmatism correcting powers and off-axis positions or orientations of the astigmatism correcting axes of the toric IOL and relaxing incision that are effective to yield lower residual astigmatism than on axis correction methods. The toric IOL and relaxing incision combinations also allow the user to avoid incisions that will radially overlap with a cataract incision thereby provided improved outcomes.

17 Claims, 10 Drawing Sheets

FIG. 6

| | | | | | Recommended Lens | | | | | | |
|---|---|---|---|---|---|---|---|---|---|---|---|
| Settings - | | | | | Select Lens ... | | | | | | |
| Surgeon | Sayegh, MD, PhD | Today | 04/14/2016 | | Brand | Type | IOL Sph | Res Sph | IOL Cyl | Res Cyl | Res Angle |
| Patient | Patient Name | Surgery Date | 04/14/2016 | | Alcon | SN6AT5 | +7.00 | +0.10 | 3.00 | 0.10 | 70.2 |
| | | Eye | OD \| OS | | Alcon | SN6AT5 | +7.50 | -0.20 | 3.00 | 0.10 | 70.2 |
| Alcon | AcQ,AcT 10 | | Brands | | Alcon | SN6AT4 | +7.00 | +0.10 | 2.25 | 0.41 | 160.2 |
| Acr,bSP,fhA ... | Mon,Bi,Tri ... | | Brands | | Alcon | SN6AT4 | +7.50 | -0.20 | 2.25 | 0.41 | 160.2 |
| Toric Priority | No Preference | Lens Order | Models | | Alcon | SN6AT5 | +6.50 | +0.39 | 3.00 | 0.10 | 70.2 |
| Sphere Formula | SRK/T | Toricity Ratio | Max Lens Count | | Alcon | SN6AT4 | +6.50 | +0.39 | 2.25 | 0.41 | 160.2 |
| Measurement | Optical | Axial Length | Material | | Alcon | SN6AT3 | +7.00 | +0.10 | 1.50 | 0.93 | 160.2 |
| | | Ant Ch Depth | Focality | | Alcon | SN6AT3 | +7.50 | -0.20 | 1.50 | 0.93 | 160.2 |
| Sphere Spec | Sph Eq Target | Sph Eq Target | Optical mm | | Alcon | SN6AT3 | +6.50 | +0.39 | 1.50 | 0.93 | 160.2 |
| K Flat | 43.00 D | Angle Flat | 0.00 D | | Alcon | SN6AT6 | +7.00 | +0.10 | 3.75 | 0.62 | 70.2 |
| K Steep | 45.00 D | Angle Steep | 73.0 ° | | | | | | | | |
| Surg Astig | 0.20 D | Incision Location | 163.0 ° | | | | | | | | |
| | | | 200.0 ° | | | | | | | | |
| | Calculate | | | | | | | | | | Print |

501 → (left panel)  502 → (right panel)

FIG. 7

501 → 502 → 701 → (brands dropdown list)

METHODS FOR SELECTING INTRAOCULAR LENSES AND RELAXING INCISIONS FOR CORRECTING REFRACTIVE ERROR

CROSS-REFERENCE TO RELATED APPLICATIONS

This application claims priority to U.S. Provisional Patent Ser. No. 62/149,539 filed Apr. 18, 2015, which is incorporated herein by reference in its entirety.

BACKGROUND

Astigmatism results from refractive errors caused by an asymmetric or irregularly shaped cornea or changes in the curvature of the lens inside the eye affecting the bending or refraction of light in the eye. Astigmatism usually causes blurred or distorted vision at all distances and where uncorrected, can lead to eyestrain, headaches and fatigue with prolonged visual tasks. It has been reported that up to 95% of eyes have some amount of astigmatism, with more than 28% of children between the ages of 5 to 17 and about 15% to 30% of adults have astigmatism of 1 diopter or greater. See J. B. Rubenstein, Today's Peripheral Corneal Relaxing incision, in Cataract & Refractive Surgery Today, pages 26-28, May 2014.

Astigmatism can be corrected during cataract surgery by placing the natural lens with a correcting toric intraocular lens (IOL) or through relaxing the curvature of the cornea by making paired arcuate incisions in the limbus or cornea of the eye using procedures such as limbal relaxing incision (LRI), astigmatic keratotomy (AK) or femtosecond laser assisted astigmatic keratotomy (fAK). These act to compensate for the corneal astigmatism and astigmatism resulting from the cataract incision(s). Current methods to correct astigmatism have limited effectiveness, as use of relaxing incisions is not always possible due to interfering cataract incisions, and both relaxing incision and toric IOLs usually provide only discrete astigmatism correcting power.

SUMMARY OF THE INVENTION

The present disclosure provides methods, tools, and systems for selecting intraocular lens useful for correcting astigmatism. The methods, tools and systems of embodiments of the invention are not limited by the discrete astigmatism correcting power of existing toric IOLs, alignment with the main axis of astigmatism to be corrected, or the position of interfering cataract incisions.

In one aspect, the invention provides a method for selecting a toric intraocular lens (IOL) and a relaxing incision combination effective to correct astigmatism when the toric IOL is implanted in an eye in a first off-axis orientation in combination with placement of the relaxing incision in a second off-axis position. The method involves: (a) receiving a predetermined magnitude for the astigmatism to be corrected; and (b) identifying a toric IOL-relaxing incision combination, wherein the toric IOL has a first astigmatism correcting power and the relaxing incision has a second astigmatism correcting power, the combination of any two of the first astigmatism correcting power, the second astigmatism correcting power, and the magnitude of astigmatism being corrected is greater than the first astigmatism correcting power, the second astigmatism correcting power, or the magnitude of astigmatism not in the combination.

In some embodiments, the astigmatism to be corrected includes surgically induced astigmatism. In some embodiments, the first astigmatism correcting power is the astigmatism correcting power of the IOL at the corneal plane. In some embodiments, the astigmatism correcting power of the IOL at the corneal plane is determined using anatomical distances within the eye. In some embodiments, the toric IOL is further selected based on residual sphere value, residual astigmatism value, the index of refraction of the IOL, or any combination thereof. In some embodiments, the first astigmatism correcting power or the second astigmatism correcting power is about 0.25, about 0.5, about 0.75, about 1, about 1.25, about 1.5, about 1.75, about 2, about 2.25, about 2.5, about 2.75, about 3, about 3.25, about 3.5, about 3.75, about 4, about 4.25, about 4.5, about 4.75, about 5, about 5.25, about 5.5, about 5.75, about 6, about 6.25, about 6.5, about 6.75, about 7, about 7.25, about 7.5, about 7.75, about 8, about 8.25, about 8.5, about 8.75, about 9, about 9.25, about 9.5, about 9.75, or about 10 diopters. In some embodiments, each of the first and second astigmatism correcting power is about 0.25, about 0.5, about 0.75, about 1, about 1.25, about 1.5, about 1.75, about 2, about 2.25, about 2.5, about 2.75, about 3, about 3.25, about 3.5, about 3.75, about 4, about 4.25, about 4.5, about 4.75, about 5, about 5.25, about 5.5, about 5.75, about 6, about 6.25, about 6.5, about 6.75, about 7, about 7.25, about 7.5, about 7.75, about 8, about 8.25, about 8.5, about 8.75, about 9, about 9.25, about 9.5, about 9.75, or about 10 diopters.

In some embodiments, the method includes identifying the off-axis orientation of the toric IOL by determining the position of the astigmatism-correcting axis of the IOL relative to the main axis of astigmatism using the first astigmatism correcting power, the second astigmatism correcting power, and the magnitude of astigmatism.

In some embodiments, the method further involves identifying the off-axis position of the relaxing incision by determining the position of the astigmatism-correcting axis of the relaxing incision relative to the main axis of astigmatism using the first astigmatism correcting power, the second astigmatism correcting power, and the magnitude of astigmatism.

In some embodiments, the position of the astigmatism-correcting axis of the IOL, the position of the astigmatism-correcting axis of the relaxing incision, or both are determined using the law of cosines. In some embodiments, the astigmatism-correcting axis of the IOL is less than 180 degrees relative to the main axis of astigmatism, and the astigmatism correcting axis of the relaxing incision is more than 180 degrees relative to the main axis of astigmatism to be corrected. In some embodiments, the astigmatism-correcting axis of the IOL is more than 180 degrees relative to the main axis of astigmatism, and the astigmatism-correcting axis of the relaxing incision is less than 180 degrees relative to the main axis of astigmatism to be corrected.

In some embodiments, the relaxing incision intersects one or more meridians distinct from one or more meridians intersecting an incision for IOL implantation.

In some embodiments, the first astigmatism correcting power, the off-axis position of the toric IOL, the second astigmatism correcting power, the off-axis position of the relaxing incision, or any combination thereof is identified using a pair of vectors, the vector sum of which comprises a magnitude and direction approximating the magnitude and axis of the astigmatism to be corrected, wherein: (a) one vector of the pair of vectors has a magnitude that corresponds to the astigmatism correcting power of the IOL and an angle, relative to the vector sum, that is twice the angle of the off-axis position of the IOL; and (b) the other vector of the pair has a magnitude that corresponds to the astigmatism correcting power of the relaxing incision and an angle, relative to the vector sum, that is twice the angle of the off-axis position of the relaxing incision.

In some embodiments, the toric IOL-relaxing incision combination provides a theoretical residual astigmatism of less than about 0.5 diopters. In some embodiments, the tonic IOL-relaxing incision combination provides a theoretical residual astigmatism approaching 0 diopters.

In another aspect, the invention provides a method for determining a post-operative corrective lens prescription for an astigmatic eye that involves determining the difference between (a) the magnitude and direction of the astigmatism to be corrected, and (b) the magnitude and direction of the vector sum as described herein, wherein the difference corresponds to the post-operative corrective lens prescription for the astigmatic eye. In some embodiments, the astigmatism to be corrected includes surgically induced astigmatism. In some embodiments, the magnitude of the vector sum includes the effective astigmatism correcting power of the lens at the corneal plane.

In another aspect, the invention provides a corrective lens having a prescription determined as described herein.

In another aspect, the invention provides a method for marking the eye that involves receiving the toric IOL-relaxing incision combination identified as described herein, and marking on the eye, the position of the astigmatism correcting axis of the IOL, the position of the astigmatism correcting axis of the relaxing incision, or both positions of the astigmatism correcting axes.

Any feature or combination of features described herein are included within the scope of embodiments of the present invention provided that the features included in any such combination are not mutually inconsistent as will be apparent from the context, this specification and the knowledge of one of ordinary skill in the art.

Unless otherwise defined, all technical and scientific terms used herein have the same meaning as commonly understood by one of ordinary skill in the art to which this invention belongs. In case of conflict, the present specification, including definitions, will control. In addition, the materials, methods, and examples are illustrative only and not intended to be limiting. Although methods and materials similar or equivalent to those described herein can be used to practice the invention, suitable methods and materials are described below.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Other features and advantages of the invention will be apparent from the following detailed description and from the claims.

BRIEF DESCRIPTION OF THE FIGURES

FIG. 4 illustrates a calculator system accordingly to an embodiment of the present invention.

FIGS. 5-11 illustrate the graphical user interface of the calculator tool that can be used to select one or more toric IOLs or relaxing incision.

DETAILED DESCRIPTION OF THE INVENTION

Figure 1A:
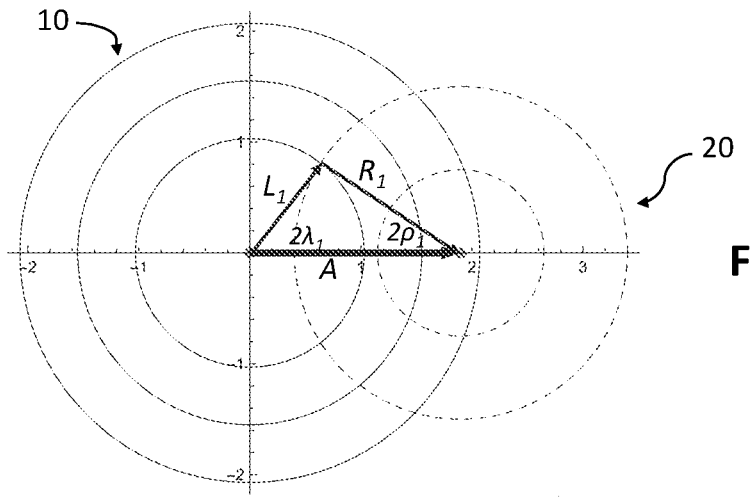
FIGS. 1A-1J are graphical representations of the vector addition method that can be use to select the astigmatism correcting power and locations of toric IOL and relaxing incision for an amount of astigmatism and location to be corrected in which each of FIGS. 1A-1J represents a possible solution for given astigmatism "A".

The invention provides methods, tools, and systems for selecting intraocular lens (IOL), relaxing incision, and IOL-relaxing incision combinations effective for correcting astigmatism. The methods, tools and systems of the invention do not require alignment with the main axis of astigmatism to be corrected and allow for positions of astigmatism correction that do not overlap with positions of cataract incisions.

In one embodiment, the invention provides a method of performing a surgical procedure for correcting astigmatism. Astigmatism in an eye can be corrected by identifying the magnitude and axis of astigmatism to be corrected, performing an implantation of a toric intraocular lens (IOL) in the eye at a first off-axis position in combination with relaxing incision in the limbus or cornea of the eye at a second off-axis position.

Corneal or lenticular astigmatism refers to differing curvature of different meridians of the anterior or posterior surface of the cornea or the lens that result in impaired vision. Astigmatism can be inherited, develop over time, develop in association with diseases such as keratoconus, or occur as a result of surgery. The term "astigmatism," as used herein, refers to a distortion in the shape of the cornea or lens that results from or is associated with eye surgery, a disease affecting the eye, or the natural shape of the cornea or lens, and thus includes corneal astigmatism, lenticular astigmatism, as well as pre-operative astigmatism and surgically induced astigmatism (e.g. due to cataract surgery). Thus, the astigmatism to be corrected in an exemplary method of the invention can be the net astigmatism resulting from pre-operative and surgically induced astigmatism, and astigmatism is corrected by a method of the invention if astigmatism determined using methods known to those skilled in the art is shown to be reduced or if vision acuity related to astigmatism reduction is improved by a detectable amount.

An astigmatism to be corrected can be identified and measured using any methods and tools known to those skilled in the art for detecting and measuring astigmatism. Non-limiting examples include retinoscopy or autorefraction (e.g. to determine refractive error), manual refraction using a phoropter (e.g. to determine magnitude and axis), wavefront (aberrometry) refraction, keratometry (e.g., measuring curvature of the steepest and flattest meridians using a keratometer), and topography (e.g. determining shape using a corneal topographer). See for example, Alpins N. & Stamatelatos G. (2014) Measuring Astigmatism, Planning Surgery and Tracking Results. In Limbal Relaxing incision, A Practical Guide. Nichamin L and Parekh P Editors. Slack Inc.

Astigmatism to be corrected can be identified by its magnitude (i.e. amount) in diopters (D) and its orientation defined by the location of its steep axis. As used herein, the term "axis of astigmatism," "main axis," "main axis of astigmatism," refers to the steep axis of astigmatism to be corrected.

In a method of the invention, astigmatism can be corrected by implanting a toric IOL in an off-axis position, i.e., a position that does not align with the identified main axis of astigmatism (i.e. the main axis of astigmatism to be corrected). Toric IOLs are well known to those skilled in the art and can be obtained from various sources including, for example, Alcon Labs (Forth Worth, Tex.), Staar Surgical (Monrovia, Calif.), Abbott Medical Optics, Inc. (Santa Ana, Calif.), Bausch & Lomb (Bridgewater, N.J.), Carl Zeiss Meditec (Jena, Germany), and Physiol (Liege, Belgium). Toric IOLs can be implanted inside the eye to replace the eye's natural lens to correct astigmatism, nearsightedness or farsightedness or without removing the natural lens as a "phakic IOL." Toric IOLs are constructed with meridians or axis having different astigmatism correcting powers or cylinder powers measured in diopters (D). Non-limiting examples of astigmatism correcting powers provided by toric IOLs include those having cylinder power about (i.e., within 15% of, or + or −15% of) 0.25, about 0.5, about 0.75, about 1, about 1.25, about 1.5, about 1.75, about 2, about 2.25, about 2.5, about 2.75, about 3, about 3.25, about 3.5, about 3.75, about 4, about 4.25, about 4.5, about 4.75, about 5, about 5.25, about 5.5, about 5.75, about 6, about 6.25, about 6.5, about 6.75, about 7, about 7.25, about 7.5, about 7.75, about 8, about 8.25, about 8.5, about 8.75, about 9, about 9.25, about 9.5, about 9.75, or about 10 diopters at the IOL plane, each of which has a cylinder power at the corneal plane of about ⅔ the cylinder power at the IOL plane. The exact ratio of astigmatism at the IOL plane to astigmatism at the corneal plane may vary, and this ratio can be determined using a method of the invention and is detailed in what follows.

A toric IOL is identified by its astigmatism correcting power (cylinder power) at an identified axis on the IOL (cylinder axis). The cylinder axis identified on the toric IOL allows for alignment of the toric IOL relative to the axis of astigmatism to be corrected to facilitate positioning the IOL at a select orientation inside the eye for optimal astigmatism correction. A toric IOL is in rotational alignment with the steep or main axis of astigmatism if the toric IOL is positioned so that its cylinder axis is on the steep or main axis of astigmatism thus reducing or neutralizing it. The cylinder axis of a toric IOL is the axis of least toricity on the toric IOL. As such, the cylinder axis is the astigmatism-correcting axis. A toric IOL is in an "off-axis" position if its cylinder axis is oriented at an angle that is not zero or 180 degrees relative to the main or steep axis of astigmatism. The off-axis position of the toric IOL can be identified in degrees by measuring the angle between the cylinder axis of the toric IOL and the main or steep axis of astigmatism to be corrected. Methods for implanting a toric intraocular lens (IOL) are known to those of skill in the art. See, for example Novis, C Astigmatism and Toric Intraocular Lenses, Current Opinion in Ophthalmology, 11(1), 47-50 (2000).

A relaxing incision is a small arcuate incision or a pair of arcuate incisions made at the edge or opposite edges, respectively, of the cornea or limbus of the eye to relax the curvature of the cornea. A relaxing incision functions to relax or reduce the curvature of the cornea in the meridian intersecting the incision. A relaxing incision formed by a pair of oppositely placed, arcuate incisions relaxes or reduces the curvature of the cornea particularly along the meridian connecting the centers of the arcuate incisions. As relaxing incision can be formed at the cornea or limbus, the term "relaxing incision" include corneal relaxing incision and limbal relaxing incision. Relaxing incision can be formed using a knife, for example, a diamond knife, or a laser, for example, femtosecond laser as known to those of skill in the art. See, for example, Nichamin, L. I). Nomogram for limbal relaxing incision. *Journal of Cataract & Refractive Surgery*, 32(9), 1408 (2006); Nichamin, Louis D. (Eds.) *Limbal Relaxing incision: A Practical Guide*. 2014. Thorofare, N.J.: Slack Incorporated; and Donnenfeld, E., & Rosenberg, E. Assisting Femto Incisions with Nomograms. *Ophthalmology Management*, 19 (June 2015), 48-52 (2015).

Relaxing incision can be identified by their astigmatism correcting powers and locations. The astigmatism correcting power of a relaxing incision is determined though incision arc length as known to those skilled in the art. Non-limiting examples of astigmatism correcting power (in diopters) for incisions of various lengths are provided in the table below based on the original Donenfeld "DONO" nomogram and more recently modified for femtosecond laser corneal incisions.

| Diopters | Limbal RI-Donnenfeld Nomogram | Femtosecond Laser RI Nomogram |
|---|---|---|
| 0.5 | 1 incision, 1½ clock hrs (45° each) | 1 incision, 1 clock hr (30° each) |
| 0.75 | 2 incisions, 1 clock hr (30° each) | 2 incisions, 2/3 clock hrs (20° each) |
| 1.50 | 2 incisions, 2 clock hrs (60° each) | 2 incisions, 1&1/3 clock hrs (40° each) |
| 3.00 | 2 incisions, 3 clock hrs (90° each) | 2 incisions, 2 clock hrs (60° each) |

*Use 5° more for against-the-rule astigmatism and younger patients and 5° less for older patients The location of relaxing incision is defined by a transcorneal axis that intersects the arc center of an arcuate incision or intersects the arc centers of the pair of arcuate incisions. The location or placement of relaxing incision defines the axis of astigmatism corrected by the relaxing incision or the astigmatism-correcting axis, e.g. a transcorneal axis extending between the arc centers of a pair of incisions.

Selecting Astigmatism Correcting Power and Off-Axis Positions of Toric IOLs and Relaxing Incision The present disclosure provides a method for selecting combinations of toric IOLs and relaxing incision to correct astigmatism. The astigmatism correcting power of the toric IOL, the astigmatism correcting power of the relaxing incision, as well as the location or orientation of the toric IOL and relaxing incision can be determined prior to or at the time of the surgery. The magnitude (or amount) and location of astigmatism to be corrected can be identified using methods known to those skilled in the art. As discussed above, the astigmatism to be corrected can include pre-operative as well as surgically induced astigmatism or their combination. The astigmatism to be corrected can be a measured value, as well as an estimated value that accounts for astigmatism occurring as a consequence of incision formed during surgery, for example, during cataract surgery or for lens implantation.

Using the magnitude and position of the astigmatism to be corrected, the toric IOLs and relaxing incision can be determined so that their astigmatism correcting power and locations with respect to the main axis of astigmatism satisfies the triangle inequality theorem. More specifically, the magnitude of the astigmatism to be corrected and the magnitudes of the toric IOL and relaxing incision to be used are three values having a mathematical relationship equivalent to the mathematical relationship among the lengths of the sides of a triangle, in particular, the combined lengths of any two sides of a triangle is always longer than the third side. As such, the following triangle inequality (formula I and II) can be used to select the combination of toric IOLs and relaxing incision effective to correct astigmatism of magnitude A. The triangle inequality useful in a method of the invention can be expressed as follows:

$$|L-R| < A < L+R \quad (\text{I})$$

In equation I, the symbol ∥ denotes the absolute value of the difference between L and R (i.e. L−R); L is the magnitude of the astigmatism correcting power of the lens in diopters (D), at the corneal plane; R is the magnitude of the astigmatism correcting power of the relaxing incision in diopters (D); A is the magnitude of the astigmatism to be corrected in diopters (D); and A, L and R are all positive real numbers.

For all values of L that are greater than R (i.e. L>R), the triangle inequality can be expressed as follows:

$$L-R < A < L+R \quad (\text{IIa})$$

Similarly, if R>L then the triangle inequality can be expressed as $$R-L < A < L+R \quad (\text{IIIb})$$

And if L=R then the triangle inequality can be expressed as:

$$0 < A < L+R \quad (\text{IIc})$$

Astigmatism having magnitudes represented by values of A satisfying the triangle inequality expressed as equation I or IIa, IIb and IIc can be neutralized or countered by positioning the astigmatic reduction components, namely a toric IOL of contribution L and relaxing incision of contribution R, obliquely relative to the main axis of astigmatism.

Figure 2:
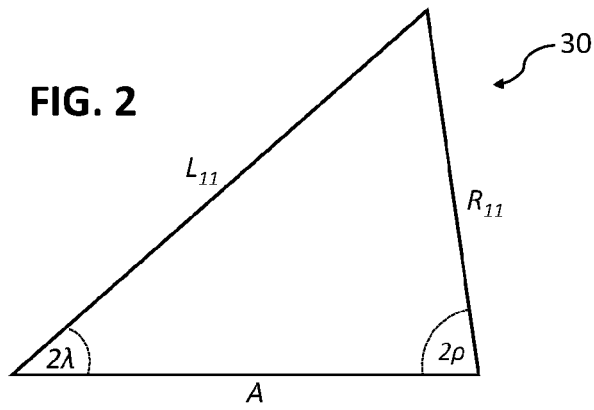
FIG. 2 is a geometric representation of a method of the invention for determining astigmatism correcting powers and off-axis locations for a toric IOL-relaxing incision combination to correct a given level of astigmatism.

The specific positions of the toric IOL and relaxing incision relative to the main axis of astigmatism can be determined using cosine and sine laws for a triangle illustrated in FIG. 2. Triangle 30 includes sides having lengths $L_{11}$, $R_{11}$ and A. If the astigmatism to be corrected has a magnitude of A, then the astigmatism correcting components (the combination of a toric IOL and relaxing incision) can have magnitudes corresponding to the values of $L_{11}$ and $R_{11}$. The off-axis positions of the astigmatism correcting components relative to the main axis of astigmatism to be corrected (i.e. A) can be determined by solving for angles $2\lambda$ and $2\rho$ of FIG. 2, and their positions relative to the main axis of astigmatism in degrees are the measures of $\lambda$ and $\rho$.

The measures of angles $\lambda$ and $\rho$ are given by:

$$\lambda = 0.5 \, \text{ArcCos}\left[\frac{(L^2 + A^2 - R^2)}{2AL}\right] \quad (\text{III})$$

$$\rho = 0.5 \, \text{ArcCos}\left[\frac{(R^2 + A^2 - L^2)}{2AR}\right] \quad (\text{IV})$$

Those cases where the triangle inequality represented by formulas I and II is barely violated i.e. A=L−R or A=L+R, correspond to flat "line" triangles. Surgically, these represent the combination of toric IOL contribution and relaxing incision contributions placed in parallel or "on axis" relative to the main axis of astigmatism to be corrected where their contributions become additive, or perpendicularly where the contribution add up but with a minus sign.

Combinations of toric IOLs and relaxing incision effective to correct a select astigmatism can be identified using vector principles applicable to the addition of two vectors, the sum of which correspond to the magnitude and direction of the astigmatism to be corrected. More specifically, the magnitude and location of the astigmatism to be corrected can be taken as the components of a resultant vector sum of two vectors: one of which corresponds to the astigmatism correcting contribution of a toric IOL and the other corresponds to the astigmatism correcting contribution of a pair of relaxing incision.

In sum, L and R represent the magnitudes of a first vector and a second vector, respectively, of a vector pair, whose sum corresponds to the vector with magnitude A (the magnitude of astigmatism to be corrected). The angles of the first and the second vectors relative to vector with magnitude A are denoted by $2\lambda$ and $2\rho$, respectively. The values of $2\lambda$ and $2\rho$ can be used to determine the off-axis locations of the toric IOL and the relaxing incision, relative to the main astigmatism to be corrected, as $\lambda$ and $\rho$ are the angles of the astigmatism correcting axes of the toric IOL and relaxing incision (the astigmatism correcting axis of the toric IOL being its cylinder axis, and the astigmatism correcting axis of the relaxing incision being defined by a trans-corneal line connecting the arc centers of a pair of arcuate incisions formed at opposite edges of the cornea).

FIGS. 1A-1F are graphical interpretations of a method of the invention. The figures provide a Cartesian plane in which the astigmatism to be corrected is represented by vector with magnitude A on the X-axis having a direction indicated by the arrow. To identify combinations of toric IOLs and relaxing incision effective to counter the astigmatism to be corrected, a first set of nested, concentric circles 10, having radii corresponding to discrete astigmatism correcting powers of available toric IOLs (L) can be overlayed at one end (the origin or tail) of the vector with magnitude A, and a second set of nested, concentric circles 20, with radii corresponding to discrete astigmatism correcting powers of defined relaxing incision (R) can be overlayed at the other end (the tip) of the vector with magnitude A. Thus, the magnitude of astigmatism to be corrected represented by the letter A is the distance between the origins of the concentric circles 10 and 20, the radius of each circle 10 represents a possible value of L (magnitude or astigmatism correcting power of a toric IOL), and the radius of each circle 20 represents a possible value of R (magnitude or astigmatism correcting power of relaxing incision). The points of intersections between a circle from each of set 10 and 20 shown in FIGS. 1A-1F represent possible combinations of L and R effective to correct astigmatism represented by vector with magnitude A, as they mark the end of a first vector (of magnitude L) beginning at the origin of circle set 10, and the beginning of a second vector (of magnitude R) ending at the origin of circle set 20. And each point of intersection of the two circles represents a particular solution combination (a particular astigmatism correcting power of toric IOL at an off-axis position, and a particular astigmatism correcting power of relaxing incision at another off-axis position) that yields zero residual astigmatism, or the desired amount of astigmatism to be corrected as incorporated in A.

Where the circles in FIGS. 1A-1J do not intersect, the values of A, R and L do not satisfy the triangle inequality theorem. That is, the combined the radii of the circles is either "too small" to bridge the gap of the astigmatism A, or one of them is "too large" and goes well beyond the point of compensating for the astigmatism A with the other component being unable to restore the "overshoot" of the first correcting term.

In sum, in a method of the invention, the astigmatism correcting power of the toric IOL and that of the relaxing incision, and the magnitude of the astigmatism to be corrected, are related as the magnitudes of a first and second vector and the magnitude of their vector sum, respectively. The astigmatism correcting axis (cylinder axis) of the toric IOL and that of the relaxing incision, measured from the axis of astigmatism to be corrected, are about half the measures of the angles of the first and the second vector relative to their vector sum, respectively. As such, the toric IOL (and its astigmatism correcting power) and that of the relaxing incision, as well as their positions relative to the axis of astigmatism to be corrected are selected so that (1) the toric IOL has a magnitude and position that correspond to the magnitude of a first vector having a first direction, (2) the relaxing incision have an astigmatism correcting power and direction that correspond to the magnitude of a second vector having a second direction, (3) the first and second vectors have a vector sum comprising a magnitude that correspond to the magnitude of the astigmatism to be corrected, and (4) the first and second vectors each having a direction that, when measured as an angle relative to the direction of the vector sum, is twice the angle of the off-axis position of the lens and incisions, respectively.

Figure 3A:
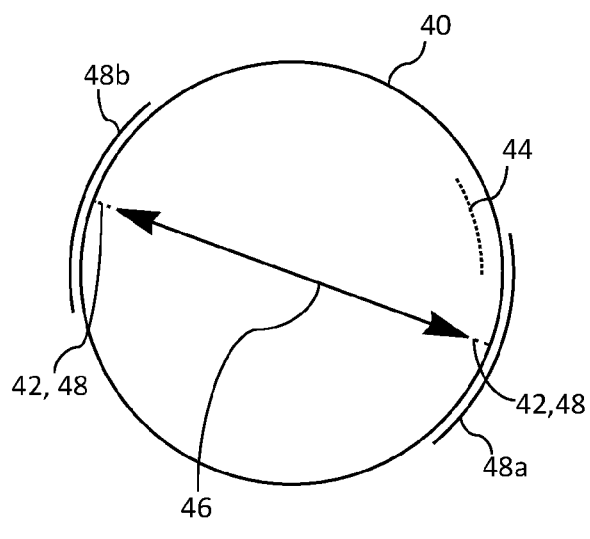
FIGS. 3A-3B are schematic diagrams of on-axis (3A) and off-axis (3B) placement of toric IOL-relaxing incision combinations.

The invention provides a method to identify a plurality of toric IOL-relaxing incision combinations that can be used to correct astigmatism of a known magnitude. The plurality of toric IOL-relaxing incision combinations allows the surgeon to select a particular combination of toric IOL-relaxing incision pairs most suitable for a particular astigmatic eye. For example, the methods of the invention can be used to determine the astigmatism correcting power of each astigmatism-correcting component in the toric IOL-relaxing incision combination, as well as the position of each component with respect to the main axis of astigmatism. As the toric IOL and relaxing incision are used in combination to apply off-axis correction of astigmatism in the eye, the toric IOL and relaxing incision are placed one on each side of the axis of astigmatism to be corrected, the positions of the toric IOL and relaxing incision on either side of the axis of astigmatism being interchangeable. For example, the toric IOL can be located in a position that is counter-clockwise from the main axis of astigmatism to be corrected, and the relaxing incision clockwise relative to the axis of astigmatism. Alternatively, the relaxing incision can be placed in a position that is counter-clockwise from the main axis of astigmatism to be corrected, and the toric IOL in a position clockwise relative to the axis of astigmatism. The counter-clockwise or clockwise position of the toric IOL and relaxing incision can be selected based on a variety of factors including: (1) level of comfort or reliability; and (2) location of cataract incision or an incision made for lens implantation or another reason. Toric IOL-relaxing incision combinations in which the astigmatism correcting components have similar astigmatism correcting powers are useful to minimize the disadvantages associated with one astigmatism-correcting component. Toric IOL-relaxing incision combinations in which the location of one astigmatism-correcting component does not overlap with another incision, e.g. cataract incisions or incisions for lens implantation, are useful in order to avoid complications associated with overlapping incisions. As used herein, the term overlapping incisions refer to incisions that intersect at least one common meridian of the eye. Overlapping incisions are illustrated in FIG. 3A for cataract incision 44 and the relaxing incision component 48a. In contrast, cataract incision 44 do not overlap with relaxing incision component 48a in FIG. 3B.

A method for identifying toric IOL-relaxing incision combinations for use in off-axis correction disclosed herein can be used to achieve residual astigmatism lower than typically achievable using on-axis treatment methods. For example, toric-IOL-relaxing incision combinations identified herein can be used in an off axis method to achieve a theoretical residual astigmatism of less than 0.4 diopters, for example, less than 0.3, 0.2, 0.1, 0.05, and near 0.04 diopters. The residual astigmatism value can be used to provide a customized, post-operative prescription for corrective lens for the treated eye using methods known to those skilled in the art.

The present disclosure also provides a method for preparing the eye for correction of astigmatism. Once a toric IOL-relaxing incision combination are obtained, their off axis positions relative to the axis of astigmatism to be corrected can be marked on the eye using, for example, a marking pen or inked marker, as well as tools such as a microscope, a fixation ring, an astigmatic ruler, or an arcuate axial marker. Methods and tools for marking the eye in preparation for performing lens transplant or relaxing incision are known to those skilled in the art. See, for example, Alpins N. & Stamatelatos G. (2014) Measuring Astigmatism, Planning Surgery and Tracking Results. In Limbal Relaxing incision, A Practical Guide. Nichamin L and Parekh P Editors. Slack Inc.; Nichamin, Louis D. (Eds.) *Limbal Relaxing incision: A Practical Guide*. 2014. Thorofare, N.J.: Slack Incorporated; and J. B. Rubenstein, Today's Peripheral Corneal Relaxing incision, in Cataract & Refractive Surgery Today, pages 26-28, May 2014.

The methods of the invention can be performed on a subject, which can be any organism within the class mammalia. Thus the term "subject" includes members in the orders carnivore (e.g., dogs and cats), rodentia (e.g., mice, guinea pigs, and rats), and primates (e.g., humans, chimpanzees, and monkeys). In some embodiments, the subject is a human. The term "humans" may include human subjects of both genders and at any stage of development (e.g., fetal, neonates, infant, juvenile, adolescent, and adult), where in certain embodiments the human subject is a juvenile, adolescent or adult. Thus, while the methods described herein may be used to perform a surgical procedure on a human subject, it is to be understood that the methods may also be used to perform a surgical procedure on other non-human subjects.

Specific embodiments of the invention are described in the following examples, which do not limit the scope of the invention described in the claims.

EXAMPLES

I. Determination of Astigmatism Correcting Power and Position for Lens Implantation and Relaxing Incision Placement Vector addition is used to determine possible combinations of (a) astigmatism correcting power of a toric IOL, (b) position of the toric IOL as defined by the astigmatism-correcting axis or cylinder axis of the toric IOL relative to the main axis of astigmatism, (c) astigmatism correcting power of relaxing incision, and (d) position of the relaxing incision as defined by an trans-corneal axis passing through the centers of the arcuate relaxing incision (i.e. arc centers) relative to the main axis of astigmatism.

The astigmatism to be corrected having diopters of about 1.9 is plotted on the x-axis as as vector with magnitude A=1.9 as shown in FIGS. 1A-1J. Existing toric IOLs with discrete diopter values of 1.03 diopters, 1.54 diopters and 2.06 diopters, for example, are plotted as solid circles 10, their centers coinciding with origin of the astigmatism vector at the origin of the Cartesian plane. Each of the three circles 10 has a radius that corresponds to the astigmatism correcting power in diopters of an existing toric IOL. Defined relaxing incision with effective discrete diopter values 0.75 and 1.50 are plotted as circles 20, their centers coinciding with the tip of astigmatism vector at 1.9 on the x-axis. The ten points of intersection formed by a circle 10 and a circle 20 (see FIGS. 1A-1J) correspond to ten possible toric IOL-relaxing incision combinations having magnitudes and positions effective to correct astigmatism of 1.9 diopters as summarized in the table below.

| Solution | Toric IOL | | Relaxing incision | |
|---|---|---|---|---|
| Combination | Power[#] | Location* | Power[##] | Location* |
| 1 (FIG. 1A) | 1.03 D | 25.9° | 1.50 D | −16.3° |
| 2 (FIG. 1B) | 1.54 D | 25.2° | 1.50 D | −26.1° |
| 3 (FIG. 1C) | 2.06 D | 22.1° | 1.50 D | −36.8° |
| 4 (FIG. 1D) | 1.54 D | 11.1° | 0.75 D | −25.4° |
| 5 (FIG. 1E) | 2.06 D | 10.7° | 0.75 D | −45.7° |
| 6 (FIG. 1F) | 1.03 D | −25.9° | 1.50 D | 16.3° |
| 7 (FIG. 1G) | 1.54 D | −25.2° | 1.50 D | 26.1° |
| 8 (FIG. 1H) | 2.06 D | −22.1° | 1.50 D | 36.8° |
| 9 (FIG. 1I) | 1.54 D | −11.1° | 0.75 D | 25.4° |
| 10 (FIG. 1J) | 2.06 D | −10.7° | 0.75 D | 45.7° |

Figure 1B:
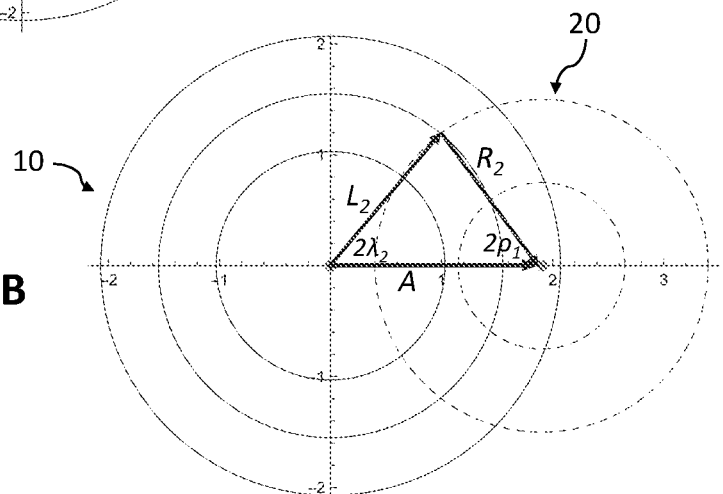
Figure 1C:
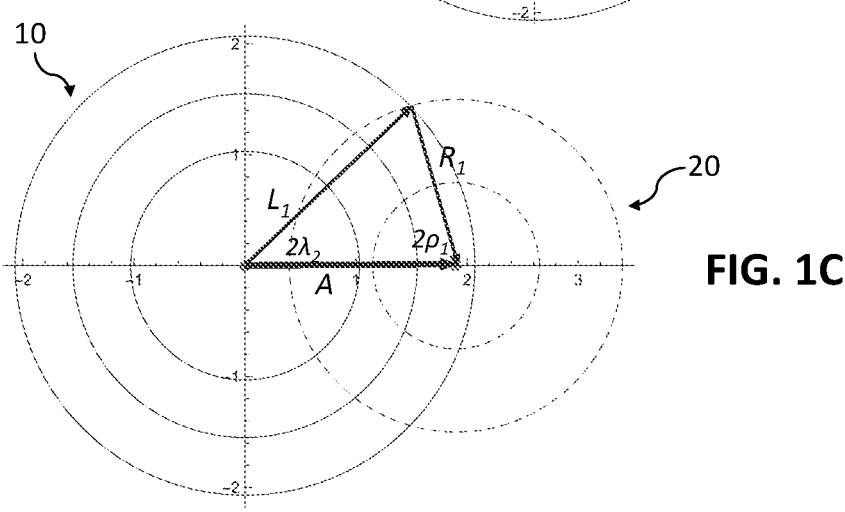
Figure 1D:
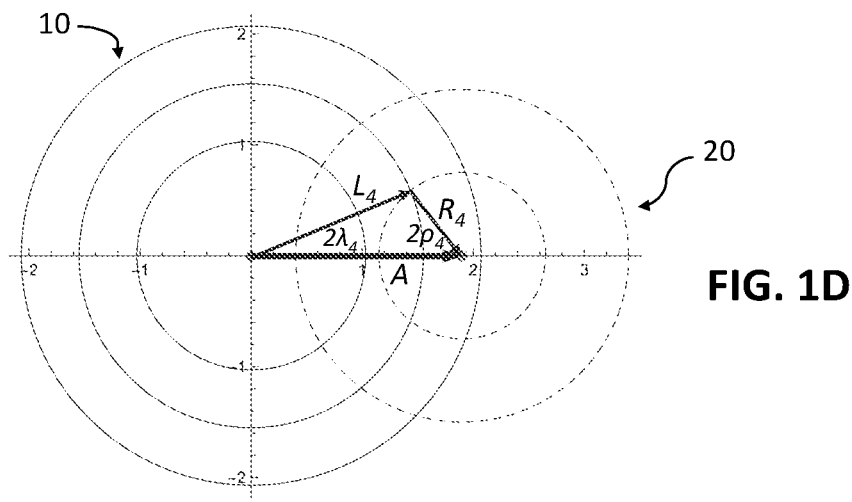
Figure 1E:
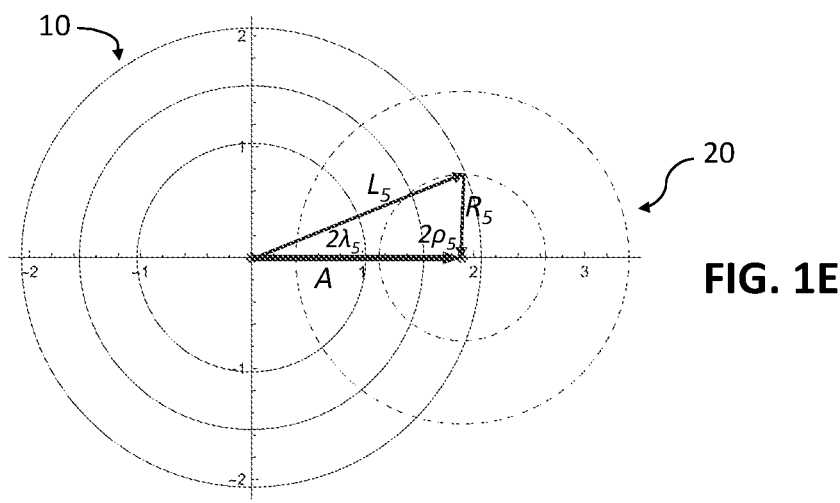
Figure 1F:
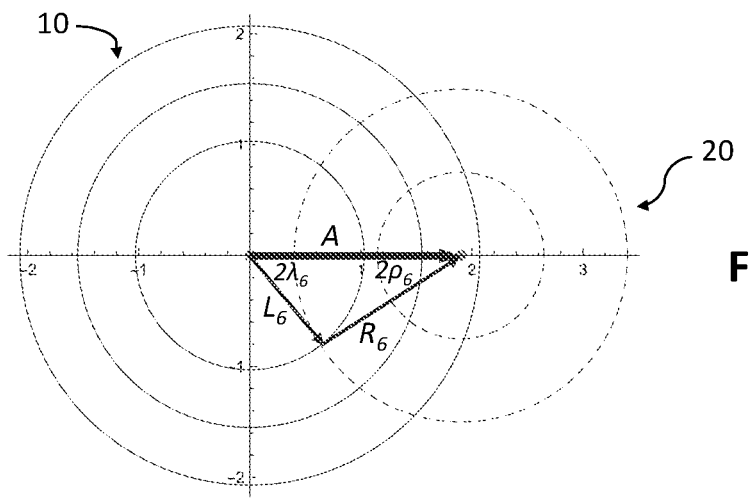
Figure 1G:
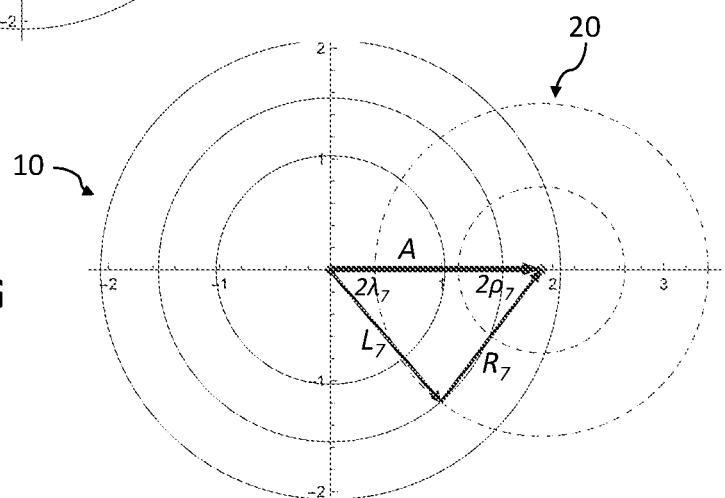
Figure 1H:
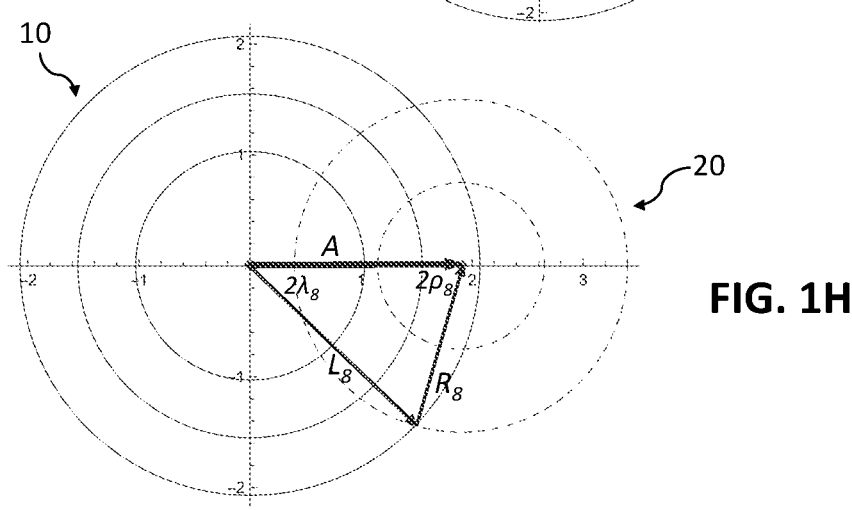
Figure 1I:
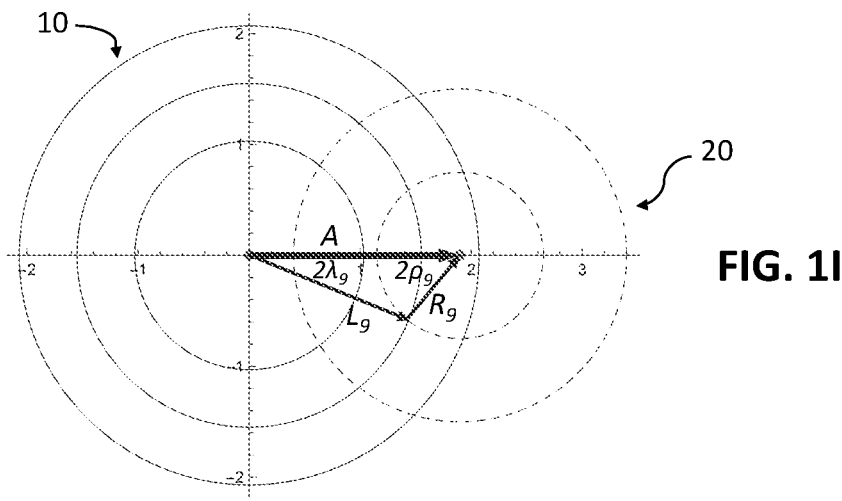
Figure 1J:
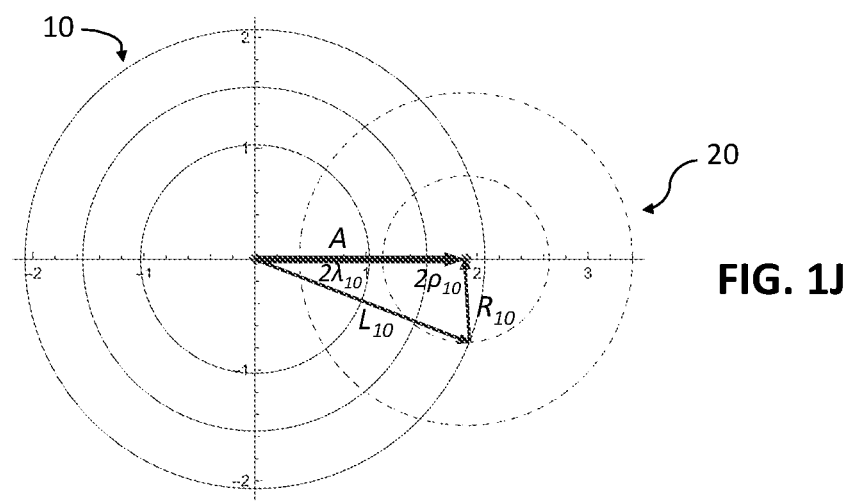

[#]astigmatism correcting power of the toric IOL at the corneal plane
*location of cylinder axis relative to the main axis of astigmatism to be corrected
[##]astigmatism correcting power of the limbal or corneal relaxing incision
**location of astigmatism correcting axis relative to the main axis of astigmatism to be corrected The graphical representations shown in FIGS. 1A-1H illustrate a plurality of solutions for correcting astigmatism of 1.9 diopters. And for each toric-IOL-relaxing incision combination, two possible arrangements of the toric IOL and relaxing incision are possible, as indicated by two points of intersection of the same two circles, one above the axis and one below the x-axis. One arrangement corresponds to the toric IOL being on a first side of the main astigmatism axis, e.g. clockwise relative to the main axis of astigmatism, and the relaxing incision being on the other side, e.g., counter-clockwise, of the main axis of astigmatism. The second arrangement corresponds the relaxing incision being on a first side of the main axis of astigmatism, e.g. clockwise relative to the main axis of astigmatism, and the toric IOL being on the other side, e.g. counter-clockwise, of the main axis of astigmatism. For example, each solution pairs illustrated in FIGS. 1A and 1F, FIGS. 1B and 1G, FIGS. 1C and 1H, FIGS. 1D and 1I, and FIGS. 1E and 1J represent astigmatism correcting contributions of L and R that have similar magnitudes but opposite directions. In FIG. 1A, the angle of L can be consider positive and that of R negative, as L and R are above the x-axis (the main axis of astigmatism). In FIG. 1F, the angle of L can be consider negative and that of R position, as L and R are below the x-axis. FIGS. 1A and 1F indicate that for each toric IOL-relaxing incision combination, the toric IOL and relaxing incision components can be arranged in two ways relative to the main axis of astigmatism. In one arrangement, the toric IOL is clockwise, while relaxing incision is counter-clockwise, relative to the main axis of astigmatism. In the other arrangement, the relaxing incision is clockwise, while the toric IOL is counter-clockwise, relative to the main axis of astigmatism. The ability to reverse the placement of the toric IOL and relaxing incision allows the surgeon to avoid forming relaxing incision that radially overlap with cataract incisions or incisions made for lens implantation, i.e. relaxing incision intersect one or more meridians of the eye that are distinct from the one or more meridians that intersect a cataract incision or incision made for any other purpose.

II. Off-Axis Implantation of a Toric IOL in Combination with Off-Axis Placement of Relaxing Incision to Maximize Range of Astigmatism Correction Astigmatisms of various diopters are corrected though modifying the off-axis orientation of a particular toric IOL-relaxing incision combination as follows. A toric IOL having an astigmatism correcting power of about 2.00 diopters at the corneal plane, for example, the Alcon "T5" (SN6AT5) or its equivalent, combined with relaxing incision having an astigmatism correcting power of about 1.5 diopters (DONON nomogram) potentially corrects astigmatism (in diopters) between a magnitude range as follows:

$$2.00-1.5<A<2.00+1.5$$

$$0.50<A<3.50$$

Positioning the astigmatism correcting axes of the toric IOL and the relaxing incision in close proximity to the main axis of astigmatism corrects astigmatism approaching 3.5 diopters, while placing the astigmatism correcting axes of the toric IOL along the main axis and the relaxing incision approaching 90 degrees from the main axis of astigmatism to be corrected neutralizes astigmatism to an magnitude approaching 0.5 diopters.

A significant majority of patients presenting for cataract surgery with astigmatism deemed correctable with good outcome falls within the range of 0.50 and 3.50 diopters.

The following table illustrates possible amounts of astigmatism correctable by such a combination and the corresponding angles.

| A | Toric IOL angle* | RI angle* |
|---|---|---|
| 0.9 | + or − 22.3° | − or + 55.2° |
| 1.4 | + or − 24.3° | − or + 43.6° |
| 1.9 | + or − 22.6° | − or + 35.5° |
| 2.4 | + or − 19.3° | − or + 28.1° |
| 2.9 | + or − 14.4° | − or + 20.0° |
| 3.4 | + or − 5.9° | − or + 7.9° |

*When the toric IOL angle is a positive value, the RI angle is a negative value. And when RI angle is a positive value, the toric IOL angle is a negative value.

As the of astigmatism-correcting axis of the toric IOL and that of the relaxing incision are positioned on different sides of the main axis of astigmatism, one in a counter-clock wise position and the other in a clock-wise position relative to the main axis of astigmatism, each combination of toric IOL-relaxing incision will include an astigmatism correcting component with a position indicated by a positive angle and a component with a position indicated by a negative angle.

As clear from the preceding description the angle of tIOL represents the position of the tIOL on one side of the axis of main astigmatism and the angle of RI is on the other side.

Each row in the table or pairs of angles corresponds thus to two distinct possible surgical choices.

III. Use of Off-Axis Implantation of a Toric IOL in Combination with Off-Axis Placement of Relaxing Incision to Minimize Residual Astigmatism This example illustrates the residual astigmatism achievable under a method of the invention. The patient has cataract in the right eye and cornea astigmatism given by 43.00 @ 73 and 45.00 @ 163 with a customary surgical induced astigmatism (SIA) of 0.20 D measuring one clock hour and centered at 210. Thus, the magnitude of astigmatism to be corrected is 2.00 diopters (45-43) at the steep axis (163 degrees) prior to accounting for SIA, and 1.95 diopters at 160 degrees after accounting for SIA (the cross cylinder or sum of corneal astigmatism and SIA). The surgeon is right handed and takes a temporal approach to the cataract surgery. The position of the surgeon is therefore at 180 degrees and the right hand uses a keratome that incises the cornea about 20 degrees to the right for a location of the cataract incision at 200 degrees. For this surgeon, an incision of about 2.4 mm results in an SIA of 0.20 diopters. This is entered in the Alcon toric calculator, UniversIOL calculator or any other calculator that combines astigmatism. The results are shown in the output of the Alcon calculator below.

The table below provides the astigmatism correcting power in diopters (D) of available toric IOLs (Alcon SN6ATx)—at the IOL plane and at the corneal plane. The Sn6ATx IOL is represented by a corresponding x in the table.

| T | IOL Plane | Corneal Plane |
|---|---|---|
| 3 | 1.5 | 1.03 |
| 4 | 2.25 | 1.54 |
| 5 | 3.00 | 2.06 |
| 6 | 3.75 | 2.57 |
| 7 | 4.50 | 3.08 |
| 8 | 5.25 | 3.60 |
| 9 | 6.0 | 4.11 |

Based on the patient's cornea astigmatism, a T4 toric IOL with astigmatism correcting power of 1.54 diopters at the corneal plane is indicated. With on-axis implantation, residual astigmatism is estimated to be about 0.40 diopters when computed using the Alcon Toric Calculator.

FIG. 3A is a schematic representation of the on-axis positions of the toric IOL and relaxing incision relative to the location of the cataract incisions. In this case, forming relaxing incision on the main axis of astigmatism results in overlap of the cataract incision with the limbal relaxing incision. Overlapping of the incisions can cause gaping and edema, in addition to making the results less predictable, is considered undesirable by a majority of surgeons and is cannot be computed by mainstream LRI calculators such as LRIcalculator.com.

As the residual astigmatism after implantation of the toric IOL is 0.40 diopters, neither the DONO nor the NAPA nomograms provides for a compensating relaxing incision, as the minimum astigmatism correcting power is 0.50 diopters for DONO and 0.75 diopters for NAPA. For example, the LRIcalculator.com, which offers an implementation of some of these nomograms, rejects requests to compute LRIs corresponding to this amount of astigmatism. While implanting a toric IOL having a lower astigmatism correcting power may allow for determining a relaxing incision contribution, one incision of the pair of relaxing incision may overlap or be very close to the location of the cataract incision and may not constitute a feasible or desirable option.

Figure 3B:
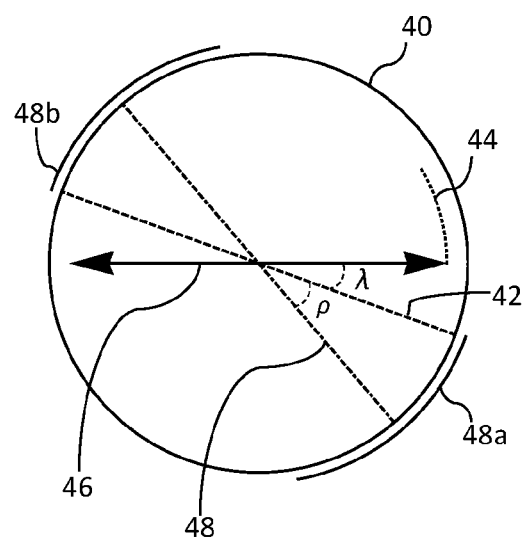

A toric IOL of the same astigmatism correcting power (1.54 diopters) is implanted in the eye in combination with relaxing incision of 1.50 diopters at off-axis positions as illustrated in FIG. 3B according to a method of the invention. The off-axis positions of the toric IOLs and relaxing incision are determined according to the triangle inequality methods of the invention, for example, as illustrated in FIG. 1B. Implantation of the toric IOL (1.54 diopters) at about 25 degrees counter-clockwise from the main axis of astigmatism to be corrected (location of cylinder axis to main axis of astigmatism to be corrected) in combination with placement of the relaxing incision about 25 degrees on the other side (clockwise) of the main axis of astigmatism to be corrected enables complete astigmatism correction, i.e. yielding a theoretical residual astigmatism approaching 0 degrees or of 0 degrees.

The oblique placement angle of the relaxing incision and/or interchangeability of the location of toric IOL and relaxing incision allow for surgical solutions that avoid overlap between cataract incisions and relaxing incision. As shown in FIG. 3B, the toric IOL is implanted at an off-axis angle occurring counter-clockwise to the main axis of astigmatism, its astigmatism correcting axis (cylinder axis) 46 being positioned between cataract incision 44 and main axis of astigmatism 42, while relaxing incision components 48a and 48b are placed on the other side (clockwise) of main axis of astigmatism 42, its astigmatism correcting axis 48 (transcorneal line connecting the arc centers of the opposite, arcuate incisions) being at an oblique, off-axis angle ρ.

The resulting residual astigmatism approaching 0 is confirmed using a vector calculator available at http://www.1728.org/vectors.htm and the following vector components inputs.

| Vector | Magnitude | Direction |
|---|---|---|
| 1-Astigmatism | 1.95 diopters | 0 degrees |
| 2-toric IOL | 1.55 diopters | 230 degrees |
| 3-relaxing incisions | 1.5 diopters | 130 degrees |

Vector 1 corresponds to astigmatism to be corrected and is designated as being at 0 degrees. As vectors 2 and 3 represent astigmatism-correcting components, their contributions acting to neutralize or counter astigmatism, their directions are opposite of vector 1 and thus determined relative to the position that is 180 degrees from the direction of astigmatism represented by vector 1 (0 degrees). And as vectors 2 and 3 are at oblique angles occurring on either side of the axis of astigmatism, their angle components being twice that of the off-axis angles of the toric IOL and relaxing incision, the angle components of vector 2 and 3 are computed as the sum and difference, respectively, of twice the off-axis angles of the toric IOL and relaxing incision as follows:

$$\text{Angle of vector } 2 = 180 + (2*25 \text{ degrees}); \text{ and} \quad (V)$$

$$\text{Angle of vector } 3 = 180 - (2*25 \text{ degrees}). \quad (VI)$$

Thus, the angle of vector 2 (with represents the toric IOL contribution) is 230 degrees relative to the main axis of astigmatism (0 degrees), and the angle of vector 3 (which represents the contribution of the relaxing incision) is 130 degrees relative to the main axis of astigmatism (0 degrees). These inputs yield a residual astigmatism of 0.039716 diopters when computed using the vector calculator (available at http://www.1728.org/vectors.htm).

IV. Method of Avoiding Incisions Overlap

The following is used to determine positioning of the toric IOL and relaxing incision in a combination so as to avoid radially overlapping incisions. The location of the main axis of astigmatism is denoted by $\alpha$. The positioning of the desired toric IOL is denoted by $\alpha +/- \lambda$, and that of relaxing incision is denoted by $\alpha -/+ \rho$. The cataract incision is denoted by iota. The arc length of relaxing incision is 2R, the arc length of the cataract incision is 2I, and $\beta = I+R$.

The 2 "limiting quantities," L1 and L2, can be determined as follows:

$$L1 = \iota - \alpha - \beta \quad (VIII)$$

$$L2 = \iota - \alpha + \beta - \pi \quad (IX)$$

There is no overlap between a relaxing incision and the cataract incision if the value of $\rho$ falls between L1 and L2. Similarly there is no overlap between a relaxing incision and the cataract incision if the value of $-\rho$ falls between L1 and L2.

Thus, if both $\rho$ and $-\rho$ are within the bracket defined by L1 and L2, then both relaxing incision configurations are non-overlapping with the cataract incision. And if both $\rho$ and $-\rho$ are outside the bracket defined by L1 and L2, then both relaxing incision configurations will overlap with the cataract incision.

The present disclosure provides a method for selecting the positions of the toric IOL and relaxing incision in a combination, and thus, allows for the inclusion or exclusion of appropriate incisions, without need for visual intervention by a surgeon or technician.

V. Computational Tool for Selecting IOL from a Variety of Available Lenses and Correcting Refractive Error and Astigmatism with One or More IOL or RI The invention provides an intraocular lens (IOL) calculator having three main components: front end 401, which can produce a graphical user interface (GUI), a computational engine 402, and a database of IOLs 403. See FIG. 4. The front end 401 receives input, manually or through communications with other measuring or storage devices, about one or more eyes and their characteristic, as well as the mode of computation and preferences. Examples of devices include web-connected devices, Ultrasound (US) or partial coherence interferometry (PCI) devices, an application dedicated to the presently described methods or a computer dedicated to the present method. The computational engine 402 includes a core calculator and perform calculations using the input from the front end 401, effectively selecting one or more IOLs and communicates with the lens database 403 in order to verify the availability and suitability of IOLs. The computational engine 402 performs ranking and filtering operations, e.g., as described herein, before returning a list of IOLs to the front end 401 that are selected and ranked according to the criteria specified by the user, e.g., through the front end or previously stored in devices connected to the front end 401, e.g., in storage configured to store criteria for ranking and filtering as described herein. The computational methods include those described herein. Other computational methods can also be used, for example, the SRKT formula and others as described in Retzlaff, J. A., Sanders, D. R., & Kraff, M. C. (1990). Development of the SRK/T intraocular lens implant power calculation formula. *Journal of Cataract & Refractive Surgery*, 16(3), 333-340; Sanders, D. R., Retzlaff, J. A., Kraff, M. C., Gimbel, H. V., & Raanan, M. G. (1990). Comparison of the SRK/T formula and other theoretical and regression formulas. *Journal of Cataract & Refractive Surgery*, 16(3), 341-346; Hoffer, K. J. (1993). The Hoffer Q formula: A comparison of theoretic and regression formulas. *Journal of Cataract & Refractive Surgery*, 19(6), 700-712; and Holladay, J. T., Musgrove, K. H., Prager, T. C., Lewis, J. W., Chandler, T. Y., & Ruiz, R. S. (1988). A three-part system for refining intraocular lens power calculations. *Journal of Cataract & Refractive Surgery*, 14(1), 17-24.

In one example, the front end 401 and the core calculator 403 can include circuitry for processing that is specifically configured to perform the method steps described herein.

Figures 4, 5:
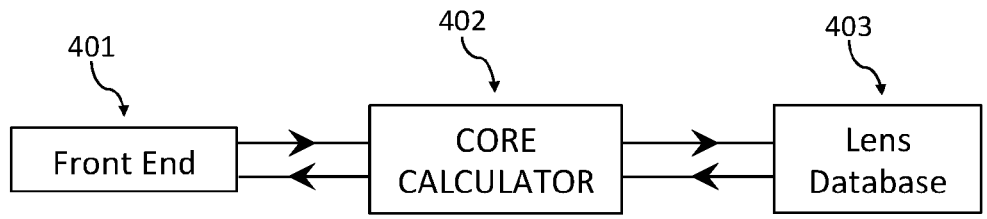

FIG. 5 illustrates input for a calculation performed for the right eye (OD) of a patient with various filtering and ranking criteria as indicated, e.g., in a first panel 501. The input can be produced by the front end 401, for example. The calculated values can be calculated at the core calculator 403 and sent to the front end 401 for display, e.g., in a second panel 502. The lower portion of the first panel 501 corresponds to the biometric information, including corneal power in two meridians and axial length with its mode of acquisition, as well as surgically induced astigmatism and its orientation.

The following include some of the possible choices corresponding to features that can be selected from the database: brands, models from each brands, maximum lens count to be ranked, material of the implants, and focality (e.g., monofocal, bifocal, trifocal, multifocal), number delivery system, lens type, add power, sphericity, geometry, material, ultraviolet (UV) block, violet light filter, recommended incision size minimum, recommended incision size maximum, haptic angle, optic diameter, overall diameter, edge, design, foldable, pieces, index of refraction, sphere minimum, sphere maximum, sphere increment, cylinder IOL plane minimum, cylinder IOL plane maximum, cylinder IOL plane increments, toricity ratio, SRK/T nominal A constant, SRK/T optical A constant, SRK/T ultrasound A constant, Holladay1 optical surgeon factor, Holladay1 ultrasound surgeon factor, Hoffer optical constant, HofferQ ultrasound constant, Haigis Optical constants, and Haigis Ultrasound constants. References, and information about date retrieved (yy/mm/dd) are also available to the user. Information on approved regions is also available and can be used to limit the search. Corresponding images for each lens are available.

Once initial criteria are selected, a ranked list of IOLs is generated using the "Select Lens" selection. In an example, the "select lens" is an actionable icon or other display device on the GUI produced by the front end 401. FIG. 6 shows the resulting ranked list in the right panel, and any element can be selected with a resulting display of its full characteristic and a description of how it fulfills the criteria specified. The resulting ranted list can be produced by the core calculator 402 using the method steps described herein, e.g., those described with reference to FIGS. 1-3. Front end 401 can display the resulting list in a bifurcated GUI with a first panel and a second panel. The first panel and the second panel can be distinct from each other. The panels can be separated by a fixed graphical element, while the panels themselves can change. The first panel can show the settings that can be used determine a lens or ranking of a plurality of lenses. The inputs into the first panel can be changed. The second panel is produced based the inputs into the first panel and in view of the rules being executed in the core calculator 402. The second panel can be the right panel.

A possible list of manufacturers is illustrated in FIG. 7 and one has been selected, here shown as Alcon. The possible list of manufactures may be a graphical element 701 that is produced from the first panel upon selection of a manufacturer's element also in the first panel. The manufacturers can be selected or deselected at will and those settings along with other settings and preferences saved for subsequent sessions.

Other input elements in the first panel can also produce a graphical element from which an input can be selected and then used for producing the results in the second panel.

Figures 8, 9:
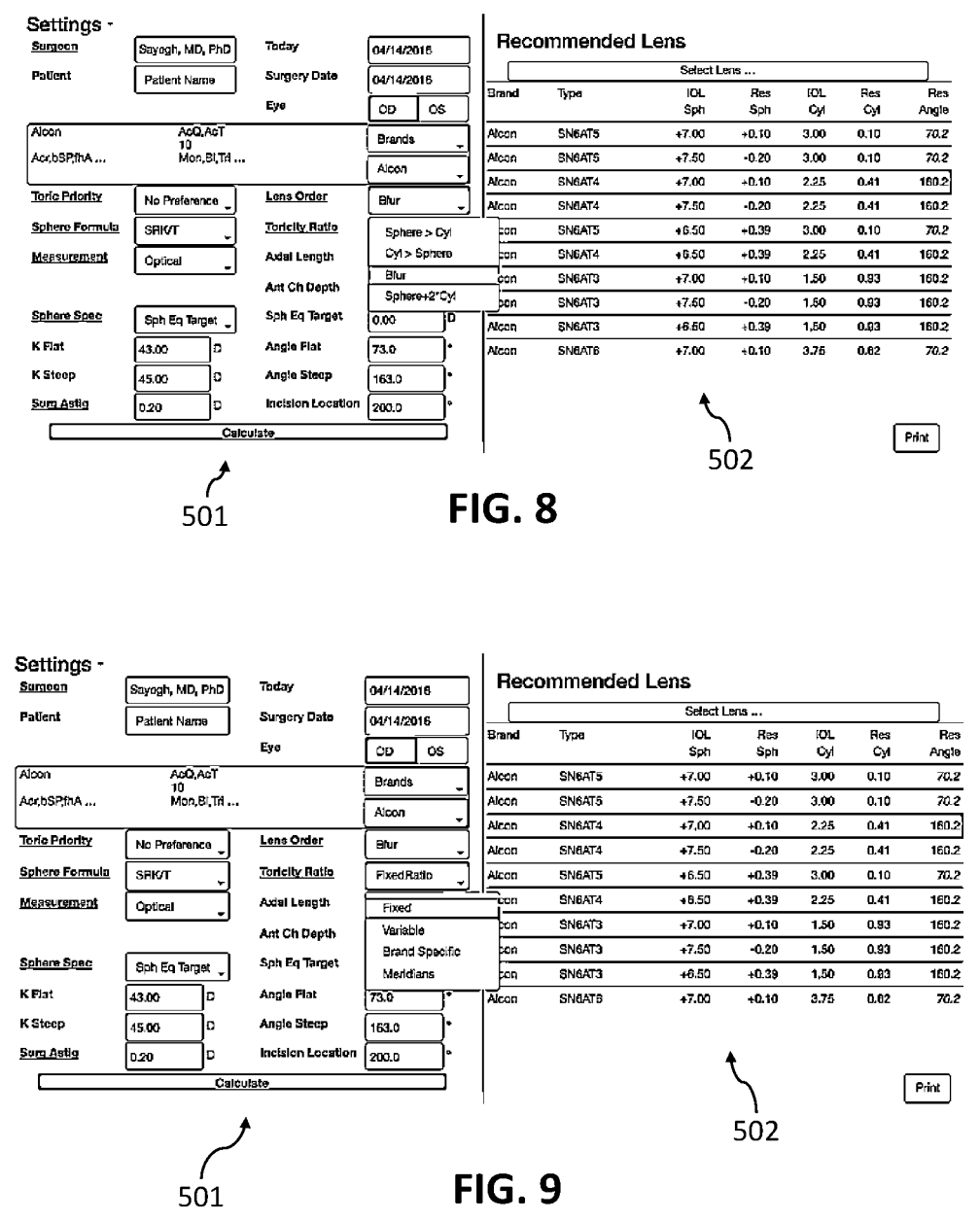

FIG. 8 illustrates the interface for selecting criteria for lens ordering. The following examples include a criterion where IOLs for which the Sphere portion of the correction is closest to target would take preference in ranking regardless of residual astigmatism. This can be shown in a graphical element in the first panel 501. The opposite criterion is listed, and a "blur" criterion [Thibos] that combines sphere and astigmatism is also illustrated as a graphical element. This later criterion is particularly powerful in the context of combined selection of sphere and astigmatic powers of an IOL.

The calculation of a toric IOL on a variety of other calculators is typically performed with a method of "fixed toricity ratio," which has been demonstrated to be inaccurate except for eyes of average anatomy. See, for example, Goggin, M., Moore, S., & Esterman, A. (2011). Outcome of toric intraocular lens implantation after adjusting for anterior chamber depth and intraocular lens sphere equivalent power effects. *Archives of Ophthalmology*, 129(8), 998-1003).

The present disclosure also provides a method to compute the toricity ratio as follows:

$$1/[(1-\varepsilon Kf)(1-\varepsilon Ks)]=\tau \qquad (VII)$$

where ε=e/n and e is the ELP or effective lens position that is computable in a known manner and in various publications for different spherical formulae. See, for example, SRK/T, Hoffer Q, Holladay 1, as listed above. In the above formula, "n" is the index of refraction of the medium (mainly aqueous humor) and can be taken to be 4/3 or other appropriate values used in the literature.

To illustrate: with Kf=Ks=40 D, ε=5 mm, τ=1/0.64~1/(⅔)=3/2=1.5, a value very close to the one used by Alcon online calculator (~1.46) despite broad approximations made here. Thus, τ will increase with increasing K and increasing e, which in turn increases with increasing axial length. This is consistent with numerical calculations made by Savinni, Hoffer et al in the context of a specific IOL formula. See Savini, G., Hoffer, K. J., Carbonelli, M., Ducoli, P., &. Barboni, P. Influence of axial length and corneal power on the astigmatic power of toric intraocular lenses. *Journal of Cataract & Refractive Surgery*, 39(12), 1900-1903)

In addition to a variable toricity ratio and the customary fixed toricity ratio, a calculator disclosed herein offers a brand-specific method (variable if brand calculator uses variable and fixed if brand calculator uses fixed) and a meridian based method (Pam, H. B., & Lim, K. L. Meridional analysis for calculating the expected spherocylindrical refraction in eyes with toric intraocular lenses. *Journal of Cataract & Refractive Surgery*, 33(12), 072-2076)) which can be selected as shown in FIG. 9.

To deduce the toricity ratio of a particular calculator, the following method is used in which: TC=Ks−Kf is the toricity at cornea; TIOL is the toricity at the IOL; RAK is the corneal residual astigmatism returned by the calculator. Thus, τ=TIOL/(TC+RAK), and t=+ where t τ is the toricity ratio and RAK is used with the appropriate sign.

Figure 10:
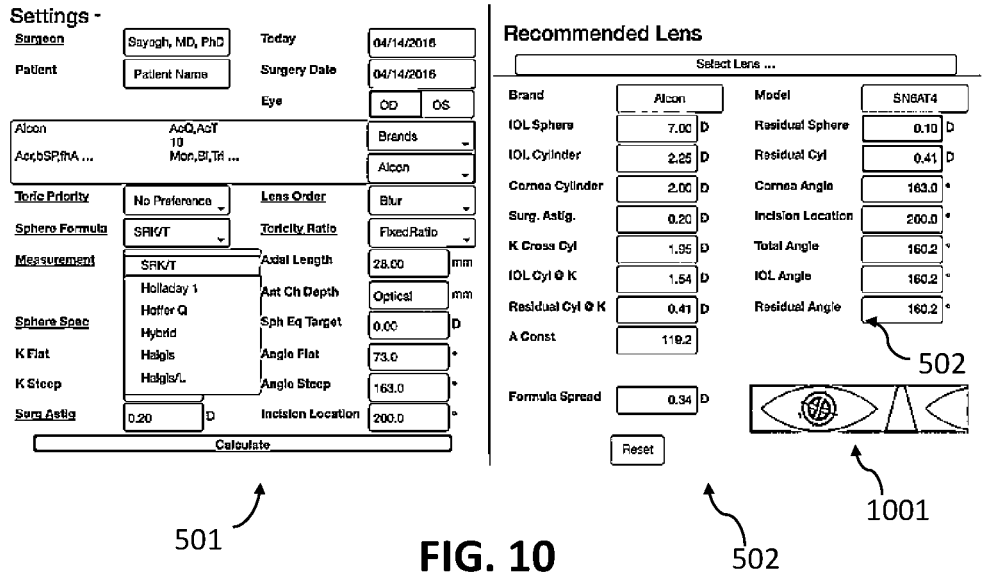

FIG. 10 illustrates a graphical user interface, e.g., in panels 501, 502, that shows a subset of a variety of calculation methods that can be used, which includes third and fourth generation methods, as well as hybrid methods to optimize outcomes and a post-LASIK method, see for example Haigis, W. (2008). Intraocular lens calculation after refractive surgery for myopia: Haigis-L formula. *Journal of Cataract & Refractive Surgery*, 34(10), 1658-1663. A multitude of post LASIK or post refractive methods can be included and integrated in the same calculator instead of being provided only in special purpose calculator like is most customary. See for example http://iolcalc.org/

This particular grouping of methods is preferable to the customary situation where different calculation methods may be distributed amongst different calculators or devices. The grouping can be shown in a graphical element in the first panel 501. These multiple methods can all be stored in computational engine 402 and individually executed when selected in the element in the first panel 501. The "formula spread" output is generated at the bottom right. It gives an indication of how the formulas differ. It is equal to the absolute value of the difference between the highest and the lowest IOL power generated. It is a reliable indicator of the predictability of the surgical outcome when a single formula is used for the calculation. The output graphic 1001 is in the second panel 502 and indicates the operated eye, incision site and positioning of the IOL when implanted.

Figure 11:
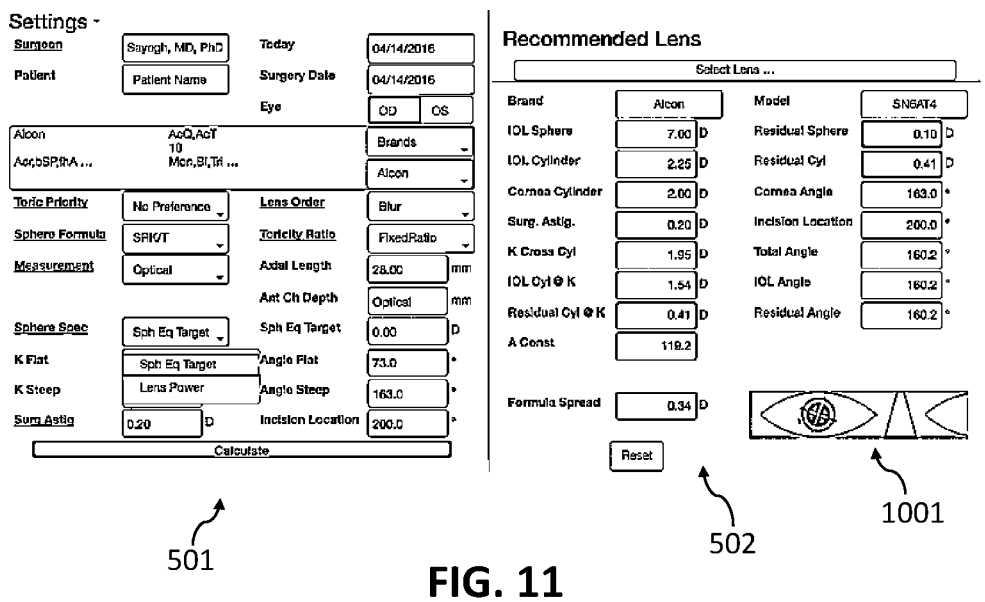
Figure 12:
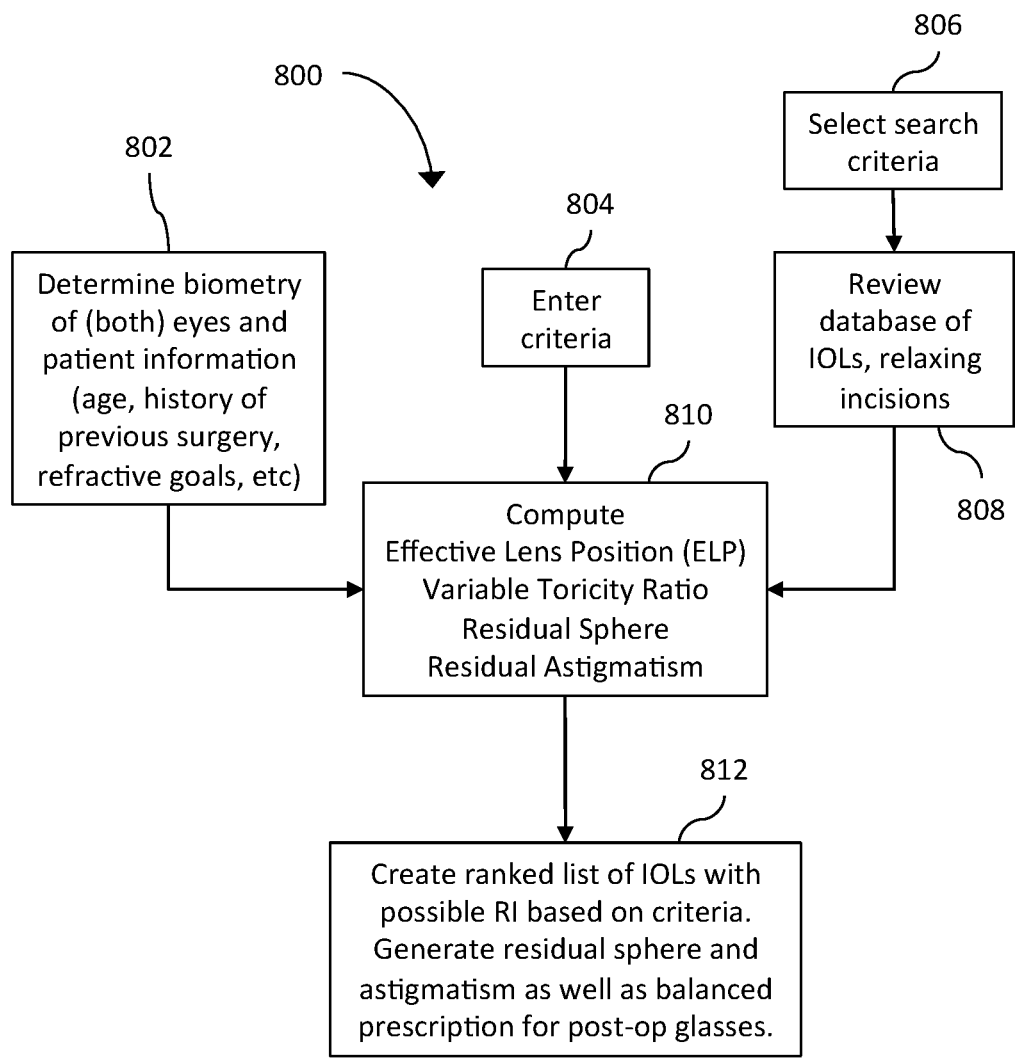
FIG. 12 illustrates a method for selecting one or more toric IOLs from a database of lenses as disclosed herein.

The sphere value of the required IOL is obtained and ported to a different calculator (or series of instructions in the computational engine 402) to compute the toric information of the required implant. This is supported in the present calculator (computational engine 402) when Lens Power is selected in the Sphere Spec field as shown in FIG. 11. The preferred simultaneous mode of calculation is also supported as indicated. FIG. 12 provides a summary of an example of a method for selecting toric IOL.

In addition to the foregoing features it is also possible to combine LRI and tIOL. The on-axis combination of LRI (limbal relaxing incision) or other incisional astigmatic reduction methods, collectively referred to as LRI or RI, is known to those skilled in the art. See, for example, Gills, J. P., Van Der Karr, M., &. Cherchio, M. (2002). Combined toric intraocular lens implantation and relaxing incision to reduce high preexisting astigmatism. *Journal of Cataract & Refractive Surgery*, 28(9), 1585-1588.

The novel approach presented here is implemented by selecting from a menu for correction of astigmatism as follows. In a first step, the user selects the number of astigmatic correction devices or interventions from the following choices: "0", "1 or less", "2 or less", or "3 or less" astigmatic correction devices/interventions. Devices or interventions include toric IOL, piggyback toric IOL, relaxing incision, or another intervention for reducing astigmatism or refractive error.

A section of 0 devices or interventions corresponds to no attempt at correcting astigmatism and will result in a non-toric IOL being selected.

For a choice of "1 or less", a choice of a toric IOL or a relaxing incision is offered, and the computations offer all solutions within the selected criteria that can be implemented with either a tIOL or a relaxing incision.

With a choice of "2 or less", solutions corresponding to 0, 1 or 2 devices or interventions are offered and ranked according to the selected criteria.

Examples of the use of two devices or interventions include: one toric IOL and one pair of relaxing incision as discussed above in the example sections; two sets of relaxing incisions; or two toric IOLs, for example, one to be implanted in the capsular bag and one to be implanted in the sulcus (piggyback).

The choice of "3 or less" proceeds in a similar manner. The methods of computations are essentially identical to the ones detailed in the examples section.

OTHER EMBODIMENTS OF THE INVENTION

While the invention has been described in conjunction with the detailed description, the foregoing description is intended to illustrate and not limit the scope of the invention, which is defined by the scope of the claims. Other aspects, advantages, and modifications are within the scope of the claims.

As used herein and in the appended claims, the singular forms "a," "an," and "the" include plural reference unless the context clearly dictates otherwise. Under no circumstances may the patent application be interpreted to be limited to the specific examples or embodiments or methods specifically disclosed herein.

Embodiments are described herein at a level of detail to allow one of ordinary skill in the art to make and use the methods, devices, systems, etc. described herein, however, variations are possible. Components, elements, and/or steps may be altered, added, removed, or rearranged. Processing steps may be added, removed, or reordered. Various embodiments are explicitly described herein; other possible embodiments that are apparent to those of ordinary skill in the art would be within the scope of embodiments of the present disclosure.

The present disclosure partitions devices and systems into multiple components, devices or steps to facilitate understanding. One or more components, devices or steps may operate as a single unit, however, and conversely, a single component, device or step can include one or more sub-components or sub-modules. The communication between the components, devices or steps can occur in a variety of ways including through hardware implementations (e.g., over a network or internal bus), instructions in dedicated hardware, or a combination of hardware and instructions. Such communications can use a variety of signals, protocols, and system architectures, such as, for example, radio signals and networks. Various forms of hardware, instruction, firmware, electronic, and optical elements, as well as various combinations of integrated circuits can be used to implement some steps of the presently described medical methods. The integrated circuits may be part of a specialized computing device designed to perform the particular functions described herein rather than by a general-purpose computer. Multiple distributed computing devices can be substituted for any one computing device illustrated herein, in which case, the functions of the one computing device are distributed (e.g., over a network) such that some functions are performed on each of the distributed computing devices. While certain embodiments are explicitly described, other embodiments are apparent to those of ordinary skill in the art based on this disclosure. Therefore, the scope of the invention is defined by reference to the claims and not simply with regard to the explicitly described embodiments.

What is claimed is:

1. A method for selecting a toric intraocular lens (IOL) and a relaxing incision combination effective to correct an astigmatism when the toric IOL is implanted in an eye in a first off-axis position in combination with placement of the relaxing incision in a second off-axis position, the method comprising:

(a) receiving a predetermined magnitude for the astigmatism to be corrected; and
(b) identifying a toric IOL-relaxing incision combination, wherein the toric IOL comprises a first astigmatism correcting power and the relaxing incision comprises a second astigmatism correcting power, and wherein the sum of any two of (i) the first astigmatism correcting power, (ii) the second astigmatism correcting power, and (iii) the magnitude of the astigmatism to be corrected is greater than the remaining one of (i) the first astigmatism correcting power, (ii) the second astigmatism correcting power, or (iii) the magnitude of the astigmatism to be corrected.

2. The method of claim 1, wherein the astigmatism to be corrected comprises a surgically induced astigmatism.

3. The method of claim 1, wherein the first astigmatism correcting power is an astigmatism correcting power of the IOL at a corneal plane of the eye.

4. The method of claim 3, wherein the first astigmatism correcting power is determined using anatomical distances within the eye.

5. The method of claim 1, wherein the toric IOL is further selected based on residual sphere value, residual astigmatism value, the index of refraction of the IOL, or any combination thereof.

6. The method of claim 1, wherein the first astigmatism correcting power or the second astigmatism correcting power is about 0.25, about 0.5, about 0.75, about 1, about 1.25, about 1.5, about 1.75, about 2, about 2.25, about 2.5, about 2.75, about 3, about 3.25, about 3.5, about 3.75, about 4, about 4.25, about 4.5, about 4.75, about 5, about 5.25, about 5.5, about 5.75, about 6, about 6.25, about 6.5, about 6.75, about 7, about 7.25, about 7.5, about 7.75, about 8, about 8.25, about 8.5, about 8.75, about 9, about 9.25, about 9.5, about 9.75, or about 10 diopters.

7. The method of claim 6, wherein each of the first and the second astigmatism correcting power is about 0.25, about 0.5, about 0.75, about 1, about 1.25, about 1.5, about 1.75, about 2, about 2.25, about 2.5, about 2.75, about 3, about 3.25, about 3.5, about 3.75, about 4, about 4.25, about 4.5, about 4.75, about 5, about 5.25, about 5.5, about 5.75, about 6, about 6.25, about 6.5, about 6.75, about 7, about 7.25, about 7.5, about 7.75, about 8, about 8.25, about 8.5, about 8.75, about 9, about 9.25, about 9.5, about 9.75, or about 10 diopters.

8. The method of claim 1, further comprising identifying the first off-axis position using the first astigmatism correcting power, the second astigmatism correcting power, and the magnitude of the astigmatism to be corrected.

9. The method of claim 8, further comprising identifying the second off-axis position using the first astigmatism correcting power, the second astigmatism correcting power, and the magnitude of the astigmatism to be corrected.

10. The method of claim 9, wherein the first off-axis position, the second off-axis position, or both the first and the second off-axis positions are determined using the law of cosines.

11. The method of claim 9, wherein the IOL comprises an astigmatism correcting axis that is less than 180 degrees relative to the main axis of the astigmatism to be corrected, and the relaxing incision comprises an astigmatism correcting axis that is more than 180 degrees relative to the main axis of the astigmatism to be corrected.

12. The method of claim 9, wherein the IOL comprises an astigmatism correcting axis that is more than 180 degrees relative to the main axis of the astigmatism to be corrected, and the relaxing incision comprises an astigmatism correcting axis that is less than 180 degrees relative to the main axis of the astigmatism to be corrected.

13. The method of claim 9, wherein the relaxing incision intersects one or more meridians distinct from one or more meridians intersecting an incision for IOL implantation.

14. The method of claim 9, wherein the first astigmatism correcting power, the first off-axis position, the second astigmatism correcting power, the second off-axis position, or any combination thereof is identified using a pair of vectors, the vector sum of which comprises a magnitude and a direction corresponding to the magnitude and the position of the main axis of the astigmatism to be corrected, respectively, wherein:

(a) one vector of the pair of vectors comprises a magnitude that corresponds to the first astigmatism correcting power and a first angle, relative to the vector sum, that is twice the angle of the first off-axis position relative to the main axis of astigmatism to be corrected; and (b) the other vector of the pair comprises a magnitude that corresponds to the second astigmatism correcting power and a second angle, relative to the vector sum, that is twice the angle of the second off-axis position relative to the main axis of the astigmatism to be corrected.

15. The method of claim 9, further comprising marking on the eye, the position of the astigmatism correcting axis of the IOL, the position of the astigmatism correcting axis of the relaxing incision, or both positions of the astigmatism-correcting axes.

16. The method of claim 1, wherein the toric IOL-relaxing incision combination provides a theoretical residual astigmatism of less than about 0.5 diopters.

17. The method of claim 1, wherein the sum of (i) the first astigmatism correcting power and (ii) the second astigmatism correcting power is greater than (iii) the magnitude of the astigmatism to be corrected.

* * * * *